| United States Patent [19] | [11] Patent Number: 4,656,161 |
|---|---|
| Herr | [45] Date of Patent: Apr. 7, 1987 |

[54] INCREASING THE ENTERAL ABSORBABILITY OF HEPARIN OR HEPARINOIDS

[75] Inventor: Dieter Herr, Altrip, Fed. Rep. of Germany

[73] Assignee: BASF Aktiengesellschaft, Fed. Rep. of Germany

[21] Appl. No.: 644,619

[22] Filed: Aug. 27, 1984

[30] Foreign Application Priority Data

Aug. 27, 1983 [DE] Fed. Rep. of Germany ....... 3331009

[51] Int. Cl.$^4$ ............................................ A61K 31/725
[52] U.S. Cl. ........................................ 514/56; 536/21
[58] Field of Search .......................... 424/183; 536/21; 514/56

[56] References Cited

U.S. PATENT DOCUMENTS

| 3,482,014 | 12/1969 | Koh | 424/183 |
|---|---|---|---|
| 3,510,561 | 5/1970 | Koh | 424/183 |
| 3,577,534 | 5/1971 | Koh et al. | 424/183 |
| 4,021,544 | 5/1977 | Nair | 424/180 |
| 4,021,545 | 5/1977 | Nair | 424/180 |
| 4,066,829 | 1/1978 | Nair | 536/103 |
| 4,156,719 | 5/1979 | Sezaki | 424/118 |
| 4,239,754 | 12/1980 | Sache et al. | 424/183 |

FOREIGN PATENT DOCUMENTS

| 0036145 | 9/1981 | European Pat. Off. ............ 424/183 |
|---|---|---|
| 1492011 | 2/1969 | Fed. Rep. of Germany . |
| 2807248 | 8/1978 | Fed. Rep. of Germany ...... 424/183 |
| 2492259 | 11/1980 | France . |
| 0138111 | 10/1981 | Japan ................................ 424/183 |
| 891554 | 3/1962 | United Kingdom ................ 424/183 |
| 1381426 | 1/1975 | United Kingdom . |
| 1563161 | 3/1980 | United Kingdom . |

*Primary Examiner*—Johnnie R. Brown
*Attorney, Agent, or Firm*—Keil & Weinkauf

[57] ABSTRACT

An enterally absorbable heparin or heparinoid preparation contains a non-ionic surfactant.

4 Claims, No Drawings

INCREASING THE ENTERAL ABSORBABILITY OF HEPARIN OR HEPARINOIDS

The present invention relates to a process for increasing the enteral absorbability of heparin or heparinoids, and the heparin or heparinoid preparation thus obtainable.

Heparin has long been known. Heparins also include low molecular weight heparins which can be prepared by a conventional method, for example fractional precipitation with a solvent, or oxidation with a periodate. Special methods, such as gel filtration (Carbohydr. Res. 51 (1976), 119 and ibid. 21 (1972), 173), partial depolymerization by esterification of the carboxyl group, followed by β-elimination (EPA No. 40,144), affinity chromatography (Thrombosis Res. 9 (1976), 575), and cleavage with peroxides (Adv. Carbohydr. Chem. 10 (1955), 359), nitrite (Carbohydr. Res. 21 (1972), 173 and Biochemistry 15 (1976), 3932) or heparinase (J. Biol. Chem. 248 (1973), 6408), and combinations of the above methods have also been employed for the preparation of low molecular weight heparin. Particular examples of heparinoids are the substances stated in Ehrhart/Ruschig: Arzneimittel, Volume 2, page 390 (Verlag Chemie, Weinheim 1972). These substances are xylan sulfate, dextran sulfate, polygalacturonic acid sulfate, polymannuronic acid sulfate, chitin sulfate, polyethylenesulfonic acid, polyanethole sulfate, polyethanol sulfate, mucopolysaccharide polysulfates and combinations of hirudine and heparin.

Heparin has been used over about the past 40 years for preventing thromboses and inhibiting blood coagulation. The great disadvantage in this context is that heparin can only be administered intravenously or subcutaneously. This considerably restricts its clinical use, and is troublesome for the hospital staff and the patient. The same applies to the heparinoids.

Attempts have been made to render heparin orally absorbable with the aid of liposomes (Belgian Pat. No. 860,011 and French Pat. No. 2,492,259), but these methods have not been adopted because of the great expense entailed, the low stability and the partially immunogenic properties of the preparations.

We have found that heparin and heparinoids can be rendered enterally absorbable by adding non-ionic surfactants.

The present invention relates to a process for increasing the enteral absorbability of heparin and heparinoids, wherein the heparin or the heparinoid is mixed with a physiologically tolerated non-ionic surfactant.

Heparins and heparinoids which can be used are those which have a mean molecular weight ($\overline{M}_w$) of from about 1,200 to about 30,000. The lower the molecular weight of the heparin or heparinoid, the greater is the absorption-promoting action of the additive. Suitable heparins also include relatively low molecular weight heparin fractions (cf. German Laid-Open Application DOS No. 2,833,898), but it should be noted in this case that heparin and heparinoid preparations having molecular weights of less than 3,000 are themselves slightly absorbable; however, the introduction of an additive results in substantially increased absorption in this case.

The heparin and the heparinoids can also be used in the form of their salts with physiologically tolerated bases, in particular the Na, Ca or Mg salts. Salts with organic bases, such as diethylamine, triethylamine or triethanolamine, are also suitable. As used in the present context, the expression heparin or heparinoid also includes the salts.

Suitable surfactants are those which are non-ionic and physiologically tolerated. These can be prepared by, for example, reacting ethylene oxide with a fatty acid, a fatty alcohol, an alkylphenol or a sorbitan or glycerol fatty acid ester, and include, for example, compounds of the formula I

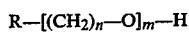

$$R-[(CH_2)_n-O]_m-H \qquad I$$

where R is alkoxy, alkylaryloxy, acylamino or acyloxy, each of 4 to 22 carbon atoms, or an acylated sorbitan or glycerol radical where the acyl radical is of 4 to 22 carbon atoms, n is an integer from 2 to 6 and m is an integer from 1 to 200. Such products are available commercially, for example under the names BRIJ®, CREMOPHOR®, MYRJ®, TRITON® and TWEEN®.

Particularly suitable surfactants of the formula I are those in which R is a hydrocarbon radical of 7 to 18, preferably 10 to 18, carbon atoms which is saturated and which carries one or more double bonds, n is 2 or 3, and m is from 10 to 100. Particular examples of these are the oxy radicals formed by eliminating hydrogen from octanol (→octyloxy), nonanol, decanol, lauryl alcohol, cetyl alcohol, isohexadecyl alcohol, oleyl alcohol or stearyl alcohol.

R may furthermore be an oxy radical of a mono-, di- or triester of a $C_4$–$C_{22}$-carboxylic acid and a $C_3$–$C_6$-polyol, such as glycerol, sorbitan or sorbitol. Further examples are oxy radicals of the ethers obtained from the stated polyols and from the alcohols corresponding to the carboxylic acids.

In addition to the radicals R stated in the Examples, specific examples are the oxy radicals of the following surfactants: sorbitol laurate, sorbitan laurate, sorbitol palmitate, sorbitan palmitate, sorbitol stearate, sorbitan stearate, sorbitol oleate, sorbitan oleate, octylphenol, nonylphenol, glycerol laurate, glycerol palmitate, glycerol stearate, glycerol oleate, glycerol hydroxylaurate, glycerol hydroxypalmitate, glycerol hydroxystearate and glycerol hydroxyoleate. Among these esters, the monoesters and diesters are preferred.

Compounds of the formula I can be obtained by, for example, reacting a compound of the formula ROH with ethylene oxide.

Other suitable surfactants are esters and ethers of, respectively, $C_4$–$C_{22}$-fatty acids or $C_4$–$C_{22}$-fatty alcohols and mono- or disaccharides. Examples of these are sucrose palmitate, sucrose palmitate stearate, mannitol oleate, octyl-β-D-glucoside nonyl-β-D-glucoside, sorbitan laurate, sorbitan palmitate, sorbitan stearate and sorbitan oleate. Mixtures of different surfactants may also be used.

The enteral absorption of the heparin or of the heparinoid begins when as little as 0.02 part by weight of surfactant per part by weight of heparin is added, and good results are obtained after the addition of 0.3–5 parts by weight of surfactant per part by weight of heparin. A larger amount of surfactant does not result in any further improvement in the absorption of the heparin or heparinoid.

The present invention furthermore relates to enterally absorbable heparin or heparinoid preparations which contain a physiologically tolerated non-ionic surfactant.

The novel heparin and heparinoid preparations are absorbed well after oral or rectal administration, are simple to prepare and are stable over a long period. This is particularly important in the case of heparin itself.

The experiments which follow illustrate the good absorption after oral administration.

A. 2 of the capsules obtained as described in Examples 1a–1d or 3a–3b (total dose 28,000 IU of heparin or 700 mg of heparinoid) were administered orally to each of a number of beagles weighing about 7 kg. The concentration of active compound in the blood of the dogs was determined before and 30 minutes, 1 hour and 2, 3, 5, 8, 14 and 24 hours after the administration of heparin. The heparin was determined in citrated plasma, using a chromogenic substrate (cf. Thromb. Res. 8 (1976), 413 and Volume 2 of Reports, Thrombosis and Hemostasis Congress, Münster, 1982, Schattauer Verlag, Stuttgart, pages 238–246). The thrombin time was also determined (cf. Kleiner Gerinnungstatus, published by Behringwerke, 1982, page 40). The heparin or heparinoid concentration (c) in the blood and the quotient T of the thrombin time of the treated animals to that of the untreated animals reached their highest values after 2 hours. Table 1 shows the data obtained 2 hours after administration.

Since, in contrast to heparin, heparinoids prolong the bleeding time (in this case the thrombin time) only slightly, if at all, they are not standardized on the basis of anticoagulant activity. Hence, dosage was according to weight, and the amount of heparinoid absorbed was stated in μg/ml of plasma.

TABLE 1

| Preparation of Example | c | T |
|---|---|---|
| 1a | 0.3 IU/ml | 2 |
| 1b | 1.2 IU/ml | 5 |
| 1c | 2.5 IU/ml | 7 |
| 1d | 8.5 IU/ml | 15 |
| 3a | 12 μg/ml | 1.4 |
| 3b | 14 μg/ml | 1.2 |

After oral administration, and without the addition of a surfactant, the heparins or heparinoids used in Examples 1a, 1b, 3a and 3b did not result in a measurable heparin or heparinoid concentration in the blood and did not change the thrombin time. The same applies to the administration of the surfactants without heparin or a heparinoid.

In the absence of added surfactant, the heparin used in Example 1c led to a heparin level of 0.15 IU/ml in the blood, but to no change in the thrombin time. The same applies to the heparin used in Example 1d, except that in this case the heparin level was 0.25 IU/ml.

B. Using a method similar to that described in A, capsules as described in Examples 2a–2n (total dose 28,000 IU of heparin) were administered to dogs, and the relative absorption-promoting action in comparison to surfactant-free preparations was measured.

We found that the surfactants increased the absorption of the heparin by a factor of from 5 to 100.

Similar data were also obtained when the heparin preparations were administered rectally. To do this, the mixtures were not introduced into capsules but were administered directly to the dogs with the aid of a bulb-headed tube.

The novel preparations can therefore be used for all indications for which heparin and the heparinoids are conventionally employed, e.g. prophylaxis of thrombosis, anticoagulation, lowering the lipid level, arteriosclerosis, and inhibiting inflammation and tumors.

The novel heparin preparation or heparinoid preparation can be administered enterally in a conventional manner, the dosage depending on the age, condition and weight of the patient. As a rule, the daily dose of active compound is from about 50 to 5,000 IU/kg of body weight, based on heparin. Normally, satisfactory results are obtained with daily doses of 100–2,000 IU/kg.

The novel heparin or heparinoid preparation may be employed in the conventional solid or liquid pharmaceutical forms, eg. tablets, film tablets, capsules, powders, granules, coated tablets or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al., Pharmazeutische Technologie, Thieme - Verlag, Stuttgart, 1978).

EXAMPLE 1

(a) 0.87 g (corresponding to 140,000 IU) of commercial heparin ($\overline{M}_w$=13,000 Dalton) was mixed with 1.3 ml of water and 0.5 g of polyethylene glycol 400 as a solubilizer, and this mixture was then mixed with 1.20 g of polyoxyethylene-20 cetyl ether (surfactant) to give a homogeneous mixture. This mixture was introduced, in equal amounts by weight, into 10 hard gelatine capsules.

Batches of 10 capsules containing heparin (14,000 IU per capsule) having a molecular weight $\overline{M}_w$ of (b) 9,000, (c) 6,000 and (d) 3,000 were prepared in a similar manner.

EXAMPLE 2

Capsules were prepared by a method similar to that described in Example 1d, using the following surfactants instead of polyoxyethylene-20 cetyl ether.
(a) Polyoxyethylene-20 stearate
(b) Polyoxyethylene-50 stearate
(c) Polyoxyethylene-20 sorbitan tristearate
(d) Polyoxyethylene-47 glycerol hydroxystearate
(e) Polyoxyethylene-23 lauryl ether
(f) Polyoxyethylene-2 cetyl ether
(g) Polyoxyethylene-16 cetyl ether
(h) Polyoxyethylene-20 stearyl ether
(i) Polyoxyethylene-20 oleyl ether
(j) Polyoxypropylene-15 stearyl ether
(k) Octylphenol polyoxyethylene-16 ether
(l) Octylphenol polyoxyethylene-30 ether
(m) Sucrose palmitate stearate
(n) Octyl-β-D-glucopyranoside

EXAMPLE 3

(a) 3.5 g of sodium pentosan polysulfate (Thrombocid ®, $\overline{M}_w$ about 4,000) were mixed with 2.5 ml of water and 0.5 g of polyethylene glycol 400 as a solubilizer, and the mixture was then mixed with 1.2 g of polyoxyethylene-20 cetyl ether (surfactant) to give a homogeneous mixture. This mixture was introduced, in equal amounts by weight, into 10 hard gelatine capsules.

(b) Capsules containing 350 mg of mucopolysaccharide polysulfate (obtained by freeze-drying the commercial product Arteparon ®, $\overline{M}_w$ about 4,300) were prepared in a similar manner.

We claim:

1. A method of preventing thrombosis and for inhibiting blood coagulation in a patient which comprises: orally administering to the patient an effective amount of a composition which consists essentially of heparin having a molecular weight of from 1,200 to about 30,000 as the active agent, at least about 0.2 part by weight of a physiologically tolerated non-ionic surfactant per part by weight of heparin and a pharmaceutically acceptable carrier and/or diluent said surfactant prepared by reacting ethylene oxide with a fatty alcohol or an alkylphenol.

2. The method of claim 1, wherein the surfactant has the formula $$R-[(CH_2)_n-O]_m-H \qquad \text{I}$$

where R is alkoxy, alkylaryloxy, acylamino or acyloxy, each of 4 to 22 carbon atoms, or an acylated sorbitan or glycerol radical where the acyl radical is of 4 to 22 carbon atoms, n is an integer from 2 to 6 and m is an integer from 1 to 200.

3. The method of claim 2, wherein R is a hydrocarbon radical of 7 to 18 carbons containing 1 or more double bonds, n is 2 or 3 and m is from 10 to 100.

4. The method of claim 1, wherein the daily amount of the composition administered to the patient is from about 50 to 5000 IU/kg.

* * * * *